(12) United States Patent
Sagel et al.

(10) Patent No.: US 6,551,579 B2
(45) Date of Patent: *Apr. 22, 2003

(54) DELIVERY SYSTEMS FOR A TOOTH WHITENER

(75) Inventors: Paul Albert Sagel, Mason, OH (US); Robert Stanley Dirksing, Cincinnati, OH (US); Frederick James Rohman, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 4 days.

This patent is subject to a terminal disclaimer.

(21) Appl. No.: 09/681,729

(22) Filed: May 29, 2001

(65) Prior Publication Data

US 2001/0053375 A1 Dec. 20, 2001

Related U.S. Application Data

(63) Continuation of application No. 09/605,220, filed on Jun. 28, 2000, which is a continuation of application No. 09/196,364, filed on Nov. 19, 1998, now Pat. No. 6,096,328, which is a continuation-in-part of application No. 09/042,909, filed on Mar. 17, 1998, now Pat. No. 6,136,297, which is a continuation-in-part of application No. 08/870,664, filed on Jun. 6, 1997, now Pat. No. 5,894,017.

(51) Int. Cl.7 .......................... A61K 7/16; A61K 7/20; A61K 9/70; A61F 13/00; A61C 13/23
(52) U.S. Cl. ......................... 424/53; 424/49; 433/215
(58) Field of Search ........................ 424/53; 433/215

(56) References Cited

U.S. PATENT DOCUMENTS

| 2,835,628 A | 5/1958 | Saffir |
| 3,070,102 A | 12/1962 | MacDonald |
| 3,625,215 A | 12/1971 | Quisling |
| 3,657,413 A | 4/1972 | Rosenthal et al. |
| 3,688,406 A | 9/1972 | Porter et al. |

(List continued on next page.)

FOREIGN PATENT DOCUMENTS

| CA | 1209761 | 8/1986 |
| CA | 2078960 | 10/1993 |
| CA | 2095445 | 7/1995 |
| CA | 2000040 | 10/1995 |
| CA | 2162536 | 5/1996 |

(List continued on next page.)

OTHER PUBLICATIONS

Messing, J.J., et al., Color Atlas of Endodontics, 1988, pp. 106–107, 135–140, 173–175, 257–259; The C.V. Mosby Company, Ltd.

Messing, J.J., et al., Color Atlas of Endodontics, 1988, pp. 106–107, 135–140, 173–175, 257–259; Wolfe Medical Publications.

(List continued on next page.)

Primary Examiner—Shep K. Rose
(74) Attorney, Agent, or Firm—James C. Vago

(57) ABSTRACT

Delivery systems for whitening teeth are provided. The delivery system includes a strip of material sized to cover a front surface of a plurality of teeth and a layer of a tooth whitening substance in contact with the strip of material. The tooth whitening substance includes a gelling agent and a whitening active selected from the group consisting of peroxides, metal chlorites, perborates, percarbonates, peroxyacids, hypochlorites, and combinations thereof. The delivery system further includes a release liner having a coating thereon, wherein the release liner exhibits less affinity for the tooth whitening substance than the tooth whitening substance exhibits for itself and for the strip of material.

23 Claims, 10 Drawing Sheets

U.S. PATENT DOCUMENTS

| | | |
|---|---|---|
| 3,754,332 A | 8/1973 | Warren, Jr. |
| 3,844,286 A | 10/1974 | Cowen |
| 3,902,509 A | 9/1975 | Tundermann et al. |
| 3,955,281 A | 5/1976 | Weitzman |
| 3,972,995 A | 8/1976 | Tsuk et al. |
| 4,138,314 A | 2/1979 | Patil et al. |
| 4,138,814 A | 2/1979 | Weitzman |
| 4,182,222 A | 1/1980 | Stahl |
| 4,211,330 A | 7/1980 | Strock |
| 4,307,075 A | 12/1981 | Martin |
| 4,324,547 A | 4/1982 | Arcan et al. |
| 4,335,731 A | 6/1982 | Bora, Jr. |
| 4,363,843 A | 12/1982 | Crofts |
| 4,376,628 A | 3/1983 | Aardse |
| 4,428,373 A | 1/1984 | Seid et al. |
| 4,431,631 A | 2/1984 | Clipper et al. |
| 4,518,721 A | 5/1985 | Dhabhar et al. |
| 4,522,805 A | 6/1985 | Gordon |
| 4,522,806 A | 6/1985 | Muhlemann et al. |
| 4,528,180 A | 7/1985 | Schaeffer |
| 4,537,778 A | 8/1985 | Clipper et al. |
| 4,544,354 A | 10/1985 | Gores et al. |
| 4,554,154 A | 11/1985 | White |
| 4,557,692 A | 12/1985 | Chorbajian |
| 4,560,351 A | 12/1985 | Osborne |
| 4,568,536 A | 2/1986 | Kronenthal et al. |
| 4,592,487 A | 6/1986 | Simon et al. |
| 4,592,488 A | 6/1986 | Simon et al. |
| 4,661,070 A | 4/1987 | Friedman |
| 4,687,663 A | 8/1987 | Schaeffer |
| 4,696,757 A | 9/1987 | Blank et al. |
| 4,713,243 A | 12/1987 | Schiraldi et al. |
| 4,728,291 A | 3/1988 | Golub |
| 4,741,700 A | 5/1988 | Barabe |
| 4,741,941 A | 5/1988 | Englebert et al. |
| 4,755,385 A | 7/1988 | Etienne et al. |
| 4,755,386 A | 7/1988 | Hsiao et al. |
| 4,770,634 A | 9/1988 | Pellico |
| 4,786,253 A | 11/1988 | Morals |
| 4,788,052 A | 11/1988 | Ng et al. |
| 4,799,888 A | 1/1989 | Golub |
| 4,812,308 A | 3/1989 | Winston et al. |
| 4,839,156 A | 6/1989 | Ng et al. |
| 4,839,157 A | 6/1989 | Mei-King Ng et al. |
| 4,849,213 A | 7/1989 | Schaeffer |
| RE33,093 E | 10/1989 | Yanagibashi et al. |
| 4,895,721 A | 1/1990 | Drucker |
| 4,900,552 A | 2/1990 | Sanvordeker et al. |
| 4,900,554 A | 2/1990 | Yanaibashi et al. |
| 4,902,227 A | 2/1990 | Smith |
| 4,919,615 A | 4/1990 | Croll |
| 4,968,251 A | 11/1990 | Darnell |
| 4,971,782 A | 11/1990 | Rudy et al. |
| 4,972,946 A | 11/1990 | Whittaker |
| 4,980,152 A | 12/1990 | Frazier et al. |
| 4,983,379 A | 1/1991 | Schaeffer |
| 4,983,381 A | 1/1991 | Zaragoza |
| 4,988,500 A | 1/1991 | Hunter et al. |
| 4,990,089 A | 2/1991 | Munro |
| 5,059,417 A | 10/1991 | Williams et al. |
| 5,076,791 A | 12/1991 | Madray et al. |
| 5,084,268 A | 1/1992 | Thaler |
| 5,098,303 A | 3/1992 | Fischer |
| 5,122,365 A | 6/1992 | Murayama |
| 5,166,233 A | 11/1992 | Kuroya et al. |
| RE34,196 E | 3/1993 | Munro |
| 5,211,559 A | 5/1993 | Hart et al. |
| 5,234,342 A | 8/1993 | Fischer |
| 5,256,402 A | 10/1993 | Prencipe et al. |
| 5,290,566 A | 3/1994 | Schow et al. |
| 5,310,563 A | 5/1994 | Curtis et al. |
| 5,326,685 A | 7/1994 | Gaglio et al. |
| 5,340,314 A | 8/1994 | Tarvis |
| 5,340,581 A | 8/1994 | Tseng et al. |
| 5,356,291 A | 10/1994 | Darnell |
| 5,376,006 A | 12/1994 | Fischer |
| 5,380,198 A | 1/1995 | Suhonen |
| 5,401,495 A | 3/1995 | Murayama |
| 5,409,631 A | 4/1995 | Fischer |
| 5,425,953 A | 6/1995 | Sintov et al. |
| 5,438,076 A | 8/1995 | Friedman et al. |
| 5,472,704 A | 12/1995 | Santus et al. |
| 5,505,933 A | 4/1996 | Norfleet et al. |
| 5,522,726 A | 6/1996 | Hodosh |
| 5,560,379 A | 10/1996 | Pieczenik |
| 5,565,190 A | 10/1996 | Santalucia et al. |
| 5,575,654 A | 11/1996 | Fontenot |
| 5,575,655 A | 11/1996 | Darnell |
| 5,611,687 A | 3/1997 | Wagner |
| 5,620,322 A | 4/1997 | Lococo |
| 5,626,866 A | 5/1997 | Ebert et al. |
| 5,631,000 A | 5/1997 | Pellico et al. |
| 5,639,445 A | 6/1997 | Curtis et al. |
| 5,662,758 A | 9/1997 | Hamilton et al. |
| 5,678,273 A | 10/1997 | Porcelli |
| 5,707,235 A | 1/1998 | Knutson |
| 5,707,736 A | 1/1998 | Levy et al. |
| 5,713,738 A | 2/1998 | Yarborough |
| 5,723,132 A | 3/1998 | Tseng et al. |
| 5,725,843 A | 3/1998 | Fischer |
| 5,746,598 A | 5/1998 | Fischer |
| 5,759,037 A | 6/1998 | Fischer |
| 5,759,038 A | 6/1998 | Fischer |
| 5,770,105 A | 6/1998 | Fischer |
| 5,780,045 A | 7/1998 | McQuinn et al. |
| 5,819,765 A | 10/1998 | Mittiga |
| 5,827,591 A | 10/1998 | Blok et al. |
| 5,846,058 A | 12/1998 | Fischer |
| 5,851,512 A | 12/1998 | Fischer |
| 5,855,870 A | 1/1999 | Fischer |
| 5,858,332 A | 1/1999 | Jensen et al. |
| 5,879,691 A * | 3/1999 | Sagel et al. .................. 424/53 |
| 5,891,453 A * | 4/1999 | Sagel et al. .................. 424/53 |
| 5,894,017 A * | 4/1999 | Sagel et al. .................. 424/53 |
| 5,922,307 A | 7/1999 | Montgomery |
| 5,953,885 A | 9/1999 | Berman et al. |
| 5,968,633 A | 10/1999 | Hamilton et al. |
| 5,980,249 A | 11/1999 | Fontenot |
| 5,985,249 A | 11/1999 | Fischer |
| 5,989,569 A * | 11/1999 | Dirksing et al. ............. 424/53 |
| 6,036,943 A | 3/2000 | Fischer |
| 6,045,811 A * | 4/2000 | Dirksing et al. ............. 424/53 |
| 6,094,889 A | 8/2000 | Van Loon et al. |
| 6,096,328 A * | 8/2000 | Sagel et al. .................. 424/53 |
| 6,136,297 A * | 10/2000 | Sagel et al. .................. 424/53 |
| 6,182,420 B1 | 2/2001 | Berman et al. |
| 6,277,458 B1 * | 8/2001 | Dirksing et al. ........... 428/42.3 |
| 6,309,625 B1 | 10/2001 | Jensen et al. |
| 6,322,360 B1 | 11/2001 | Burgio |

FOREIGN PATENT DOCUMENTS

| | | |
|---|---|---|
| CA | 2162812 | 5/1996 |
| CA | 2162885 | 5/1996 |
| DE | 1104116 | 4/1961 |
| DE | 2330869 | 1/1975 |
| EP | 0 063 604 | 4/1982 |
| EP | 0 200 508 | 12/1986 |
| EP | 0 252 459 | 1/1988 |
| EP | 0 381 194 | 8/1990 |
| EP | 0763358 A1 | 9/1996 |
| EP | 763358 * | 3/1997 |

| | | |
|---|---|---|
| GB | 1142325 | 2/1969 |
| GB | 2108841 | 5/1983 |
| JP | 6354318 | 3/1988 |
| RU | 2075965 C1 | 9/1994 |
| WO | WO 88/06879 | 9/1988 |
| WO | 95/05416 | 2/1995 |
| WO | WO 95/24872 | 9/1995 |
| WO | WO 97/25968 | 7/1996 |
| WO | 9625910 * | 8/1996 |
| WO | 9817 263 * | 4/1998 |
| WO | 2000044845 * | 8/2000 |
| WO | 2001001958 * | 1/2001 |
| WO | 2001030263 * | 5/2001 |

OTHER PUBLICATIONS

Besner, E., et al., Pratical Endodontics, 1994, pp. 7–15, 178–180; Mosby–Year Book, Inc.

S.M. Newman, et al., "Tray–Forming Technique for Dentist–Supervised Home Bleaching", Quintessence International, 1995, pp.447–453, vol. 26, No. 7.

G. McLaughlin, et al., "Materials" and "Clinical Techniques", Color Atlas of Tooth Whitening, 1991, pp.35–38 & 45–50, Ishiyaku EuroAmerica, Inc.

R.E. Goldstein, et al., "Chemistry of Bleaching", Complete Dental Bleaching, 1995, pp.25–32 & 90–97, Quintessence Publishing Co, Inc.

V.B. Haywood, et al., "Nightguard Vital Bleaching", Quintessence International, 1989, vol. 20, No. 3, pp. 173–176, 19$^{th}$ International Meeting on Dental Implants and Transplants, Bologna, Italy.

V.B. Haywood, "History, Safety, and Effectiveness of Current Bleaching Techniques and Applications of the Nightguard Vital Bleaching Technique", Quintessence International, 1992, vol. 23, No. 7, pp. 471–488.

V.B. Haywood, "Nightguard Vital Bleaching", Dentistry Today, 1997, pp.86–91.

V.B. Haywood, "Nightguard Vital Bleaching: Current Concepts and Research", JADA, 1997, vol. 128, pp. 19S–25S.

"Tooth Bleaching, Home–Use Products", Clinical Research Associates Newsletter, 1989, vol. 3, Issue 12.

Ralph H. Leonard Jr., et al, "Risk factors for developing tooth sensitivity and gingival irritation associated with nightguard vital bleaching", Esthetic Dentristy, 1997, vol.28,No. 8, pp. 527–534.

Van B. Haywood, et al, "Nightguard vital bleaching: how safe is it?", Esthetic Dentistry, 1991, vol.22, No. 7, pp. 515–523.

Van B. Haywood, "History, safety and effectiveness of current bleaching techniques and applications of the nightguard vital bleaching technique", Esthetic Dentistry, 1992, vol.23, No. 7, pp.471–488.

Van B. Haywood, "Bleaching of vital and notvital teeth", Periodontology and Restorative Dentistry, 1992, pp. 142–149.

Van B. Haywood, "Nightguard vital bleaching, a history and products update: Part 1", Esthestic Dentistry Update, 1991, vol.2, No. 4, pp. 63–66.

Van B. Haywood, "Nightguard vital bleaching, a history and products update: Part 2", Esthestic Dentistry Update, 1991, vol.2, No. 5, pp. 82–85.

Claudia Paula Drew, "Teeth Bleaching. . . a Vital technique for you to know", 1998, Sep./Oct., pp. 23–25.

Van Benjamin Haywood, "Overview and Status of Mouthguard Bleaching" Journal of Esthetic Dentistry, 1991, vol.3, No. 5, pp. 157–161.

Van B. Haywood, "Nightguard vital bleaching: current information and research", Esthetic Dentistry Update, 1990, vol. 1, No. 2, pp. 20–25.

Carolyn F. G. Wilson, et al, "Color change following vital bleaching of tetracycline–stained teeth" Pediatric Dentistry, 1985, vol. 7, No. 3, pp. 205–208.

"Tooth Bleaching, Home–Use Products", Clinical Research Associates Newsletter, 1989, pp. 1–4.

Sue Ellen Richardson, "Home bleaching: effectiveness, history, technique, bleaches, cost and safety" The Journal of the Greater Houston Dental Society, 1989, pp. 22–26.

Van B. Haywood, "Nightguard vital bleaching", Dentistry Today, 1997, pp. 88–91.

Van B. Haywood, "The food and drug administration and its influence on home bleaching", ADA, 1993, pp. 12–18.

Van B. Haywood, "Efficacy of foam liner in 10% carbamide peroxide bleaching technique", Esthetic Dentistry, 1993, vol.24, No. 9, pp.663–666.

Christopher J. Woolverton, "Toxicity of two carbamide peroxide products used in nightguard vital bleaching", American Journal of Dentistry, 1993, vol.6, No. 6, pp. 310–314.

Van B. Haywood, "Response of normal and tetracycline–stained teeth with pulp–size variation to nightguard vital bleaching", Journal of Esthetic Dentistry, 1994, vol.6, No. 3, pp. 109–114.

Ralph E. Leonard, et al, "Salivary pH changes during 10% carbamide peroxide bleaching" Dental Research, 1994, vol.25, No. 8, pp. 547–550.

Ralph E. Leonard, et al, "Change in pH of plaque and 10% carbamide peroxide solution during nightguard vial bleaching treatment" Esthetic Dentistry, 1994, vol. 25, No. 12, pp. 819–823.

Van B. Haywood, "Historical development of whiteners: clinical safety and efficacy", Aesthetics, 1997, pp.98–104.

Van B. Haywood, "Considerations and variations of dentist–prescribed,home–applied vital tooth–bleaching techniques", Compend Contin Educ Dent, 1994, Suppl.No. 17, pp. s616–s621.

Van B. Haywood, "Effectiveness, side effects and long–term status of nightguard vital bleaching", JADA, 1994, vol. 125, pp. 1219–1226.

James W. Curtis, et al, "Assessing the effects of 10 percent carbamide peroxide on oral soft tissues", JADA, 1996, vol. 127, pp. 1218–1223.

Fonda G. Robinson, et al, "Effect of 10 percent carbamide peroxide on color of provisional restoration materials", JADA, 1997, vol. 128, pp. 727–731.

Van B. Haywood, "Nightguard vital bleaching: current concepts and research", JADA, 1997, vol. 128, pp. 19s–25s.

Van B. Haywood, "Commonly asked questions about nightguard vital bleaching", IDA Journal, 1993, pp. 28–33.

Van B. Haywood, "Nightguard vital bleaching: current concepts and research", JADA, 1997, vol. 128, pp. 19s–25s.

Van B. Haywood, "Commonly asked questions about nightguard vital bleaching", The Dental Assistant, Mar./Apr. 1996, pp. 6–12.

M.S. McCracken, "Demineralization effects of 10 percent carbamide peroxide", *Journal of Dentistry*, 1996, vol. 24, No. 6, pp. 395–398.

Van B. Haywood, "Efficacy of six months of nightguard vital bleaching of tetracycline-stained teeth", *Journal of Esthetic Dentistry*, 1997, vol.9, No. 1, pp. 13–19.

Van B. Haywood, "Achieving, maintaining and recovering successful tooth bleaching", *Journal of Esthetic Dentistry*, 1996, vol.8, No. 1, pp. 31–38.

Carl M. Russell, et al, "Dentist-supervised home bleaching with ten percent carbamide peroxide gel: a six month study", *Journal of Esthetic Dentistry*, 1996, vol. 8, No. 4, pp. 177–182.

Van B. Haywood, "Historical development of whiteners: clinical safety and efficacy", *Aesthetics*, April 1997 update, pp. 98–104.

* cited by examiner

DELIVERY SYSTEMS FOR A TOOTH WHITENER

CROSS REFERENCE TO RELATED APPLICATIONS

This application is a continuation of copending U.S. application Ser. No. 09/605,220, filed Jun. 28, 2000, which is a continuation of U.S. application Ser. No. 09/196,364, filed Nov. 19, 1998, now U.S. Pat. No. 6,096,328, which is continuation-in-part of U.S. application Ser. No. 09/042,909, filed Mar. 17, 1998, now U.S. Pat. No. 6,136,297, which is a continuation-in-part of U.S. application Ser. No. 08/870,664, filed Jun. 6, 1997, now U.S. Pat. No. 5,894,017, the substances of which are incorporated herein by reference.

BACKGROUND OF INVENTION

A recognized consumer need is a low cost commercial oral care delivery system that is comfortable to wear that can deliver a sufficient amount of an oral care substance for rapid delivery of an active contained in such substance. In addition a delivery system is needed which does not require extensive user placement manipulation to be certain of good contact for optimal delivery. Furthermore, what is needed is a non-bulky active containment means that will permit the wearer to use the system during social discourse without interfering with the wearer's speech or appearance. Also needed is a containment means that will protect oral care substance from erosion from contact with other oral surfaces and, or saliva.

SUMMARY OF INVENTION

Delivery systems for whitening teeth are provided. The delivery systems include a strip of material sized to cover a front surface of a plurality of teeth and a layer of a tooth whitening substance in contact with the strip of material. The tooth whitening substance includes a gelling agent and a whitening active selected from the group consisting of peroxides, metal chlorites, perborates, percarbonates, peroxyacids, hypochlorites, and combinations thereof. The delivery systems further include a release liner having a coating thereon, wherein the release liner exhibits less affinity for the tooth whitening substance than the tooth whitening substance exhibits for itself and for the strip of material.

BRIEF DESCRIPTION OF DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements and wherein:

DETAILED DESCRIPTION

The abbreviation "cm", as used herein, means centimeter. The abbreviation "mm" as used herein, means millimeter.

Figure 1:
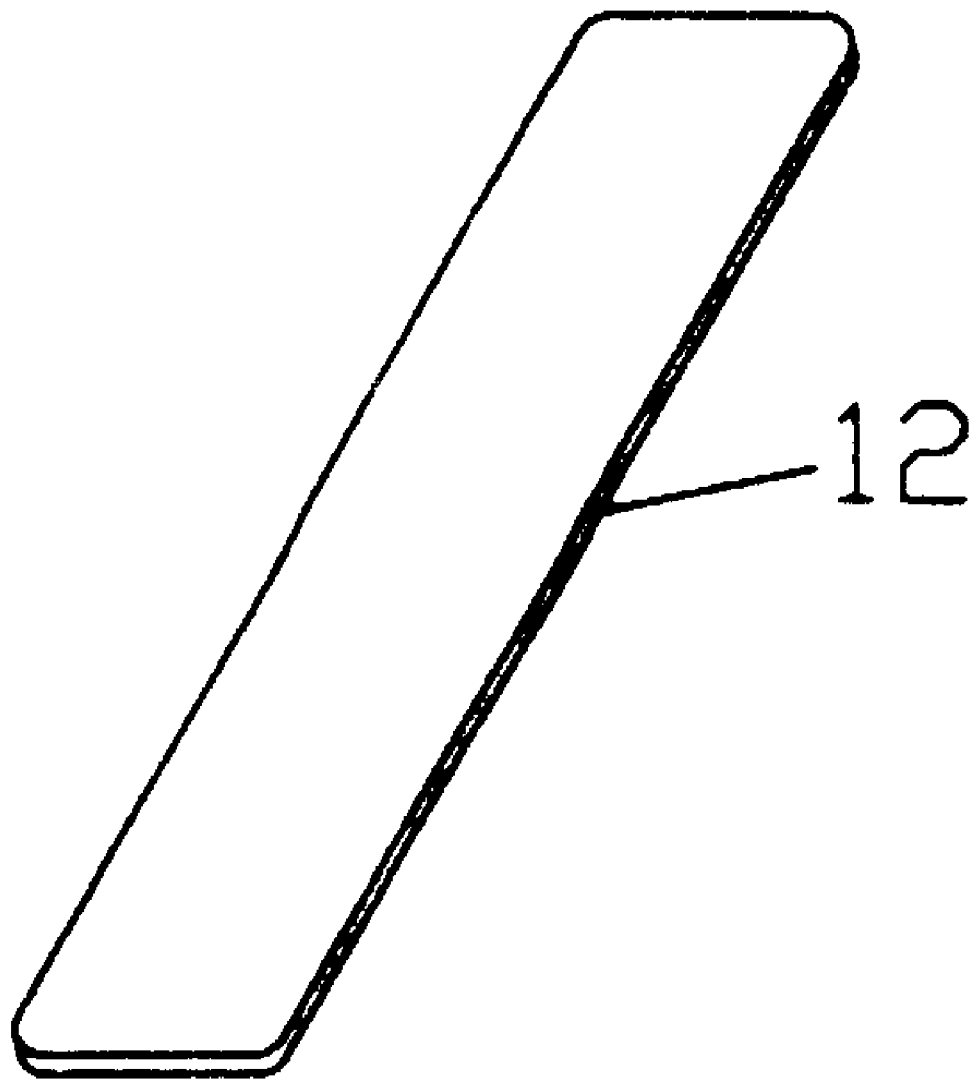
FIG. 1 is a perspective view of a substantially flat strip of material having rounded corners.
Figure 2:
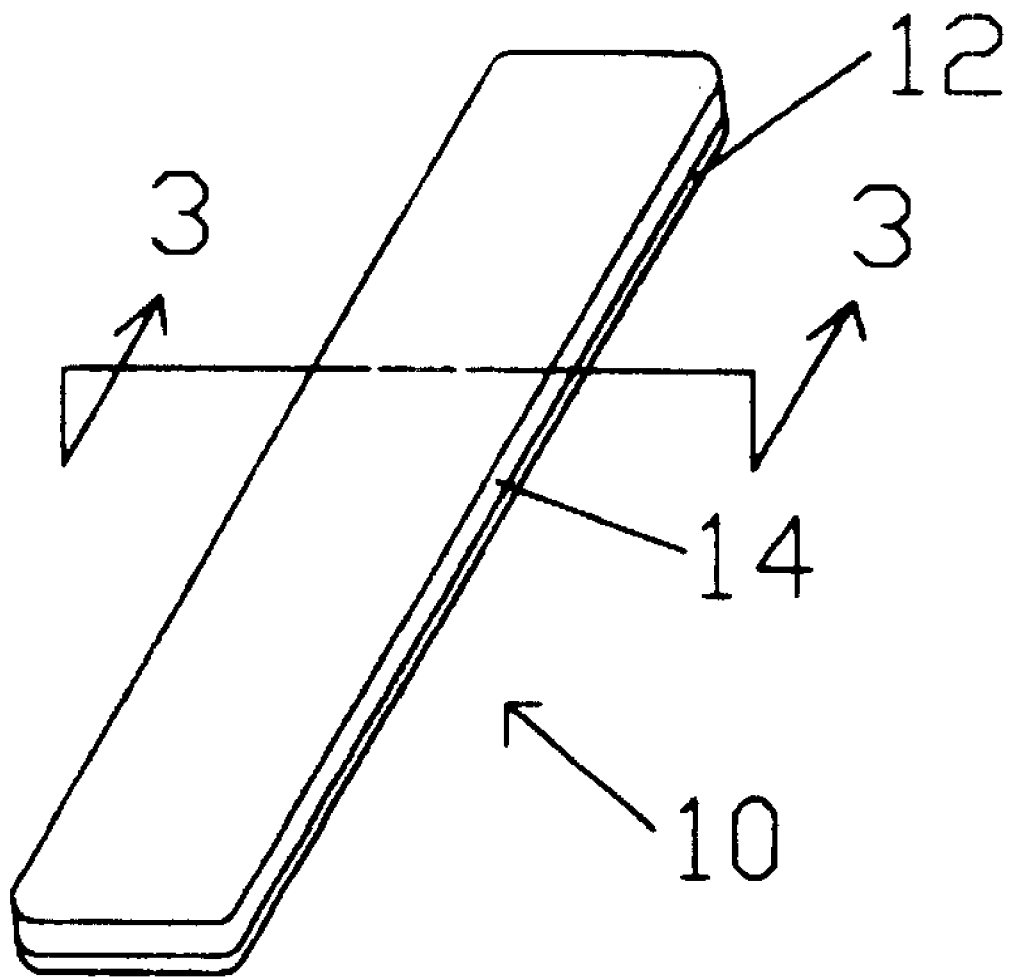
FIG. 2 is a perspective view of an embodiment of the present invention, disclosing the flat strip of FIG. 1 coated with an oral care substance for treating teeth and gums.

Referring now to the drawings, and more particularly to FIGS. 1 and 2, there is shown a first preferred embodiment of the present invention, generally indicated as 10, representing a delivery system for delivering an oral care substance to an oral surface. Delivery system 10 has a strip of material 12, which is initially substantially flat, preferably with rounded corners.

Figure 3:
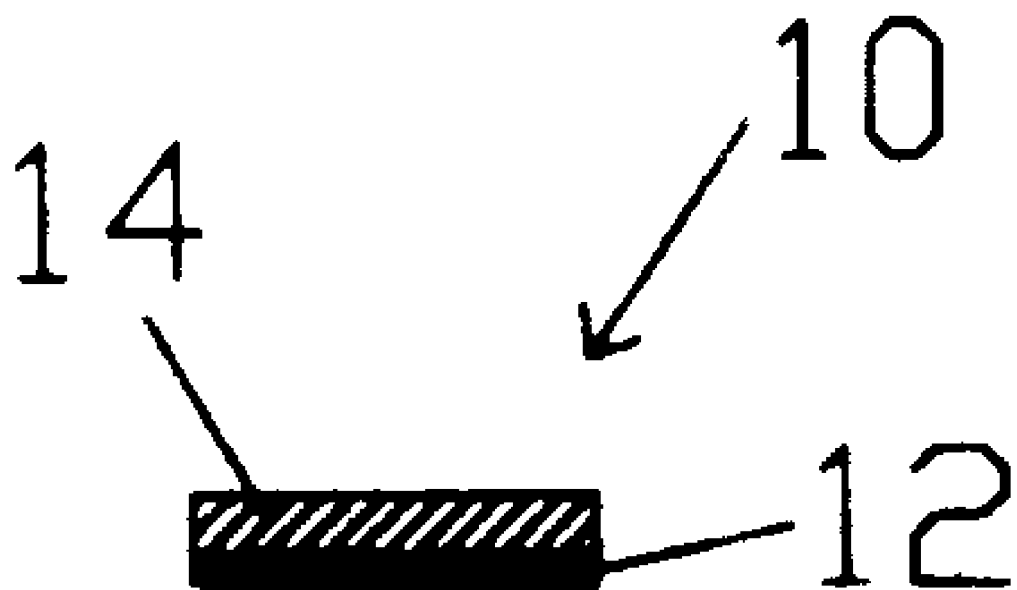
FIG. 3 is a cross-sectional view thereof, taken along section line 3—3 of FIG. 2, disclosing an example of the flat strip of material having a thickness less than that of the substance coated thereon.

Applied or coated onto strip of material 12 is an oral care substance 14. Preferably, oral care substance 14 is homogeneous, uniformly and continuously coated onto strip of material 12, as shown in FIG. 3. However, oral care substance 14 may alternatively be a laminate or separated layers of components, an amorphous mixture of components, separate stripes or spots or other patterns of different components, or a combination of these structures including a continuous coating of oral care substance 14 along a longitudinal axis of a portion of strip of material 12.

Figure 4:
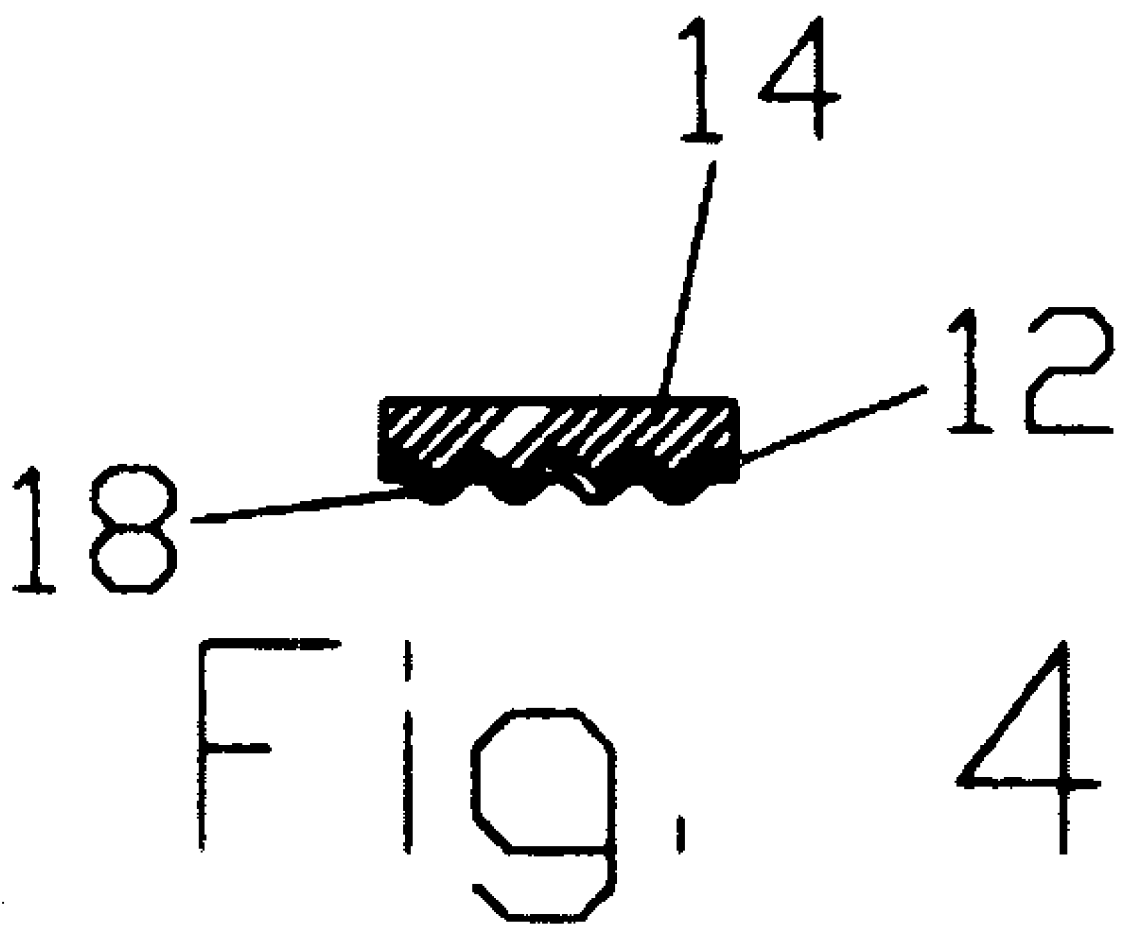
FIG. 4 is a cross-sectional view showing an alternative embodiment of the present invention, showing shallow pockets in the strip of material, which act as reservoirs for additional oral care substance coated on the strip.

As shown in FIG. 4, an alternative embodiment, a strip of material 12 may have shallow pockets 18 formed therein. When oral care substance 14 is coated on a substance-coated side of strip of material 12, additional oral care substance 14 fills shallow pockets 18 to provide reservoirs of additional oral care substance 14.

Figure 5:
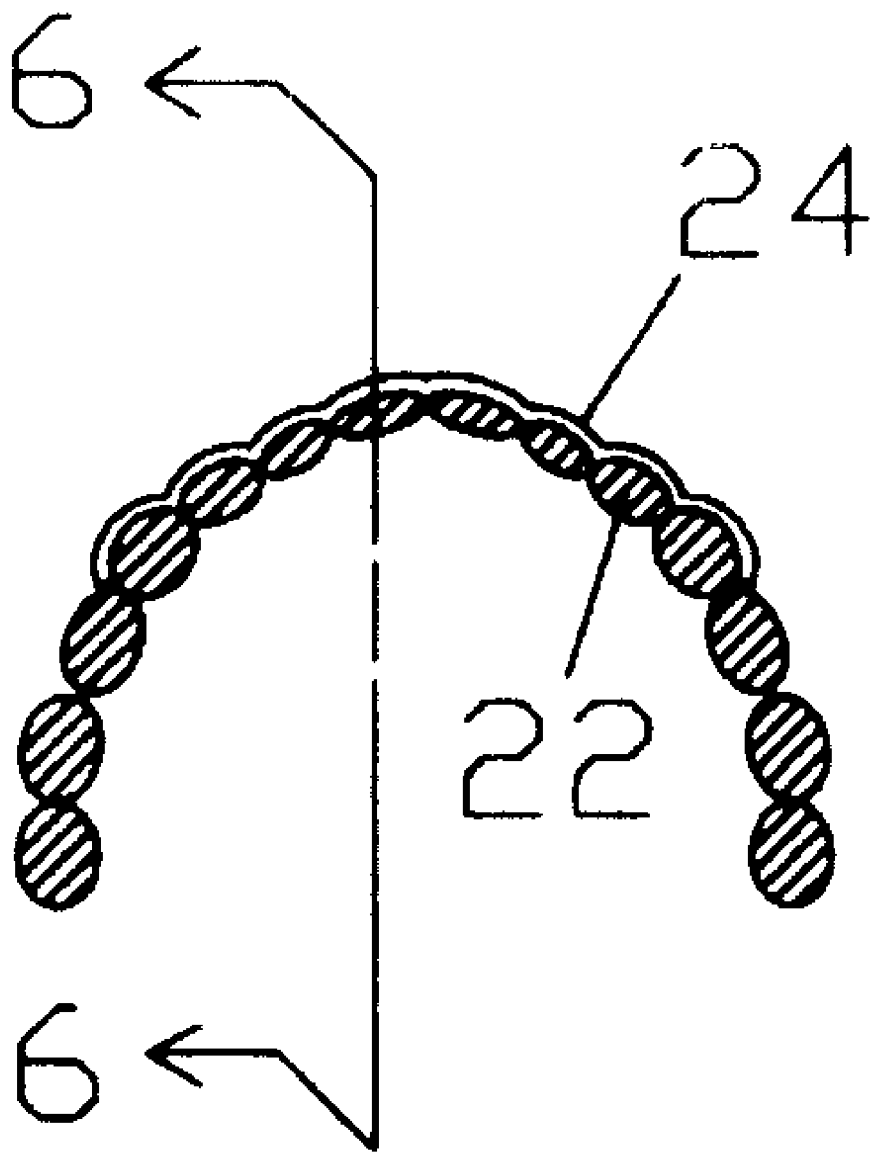
FIG. 5 is a cross-sectional plan view thereof, showing an alternative embodiment for applying oral care substances for treating teeth to adjacent teeth having the strip of material of the present invention conforming thereto and adhesively attached to the teeth by means of the oral care substance located between the teeth and the strip of material.
Figure 6:
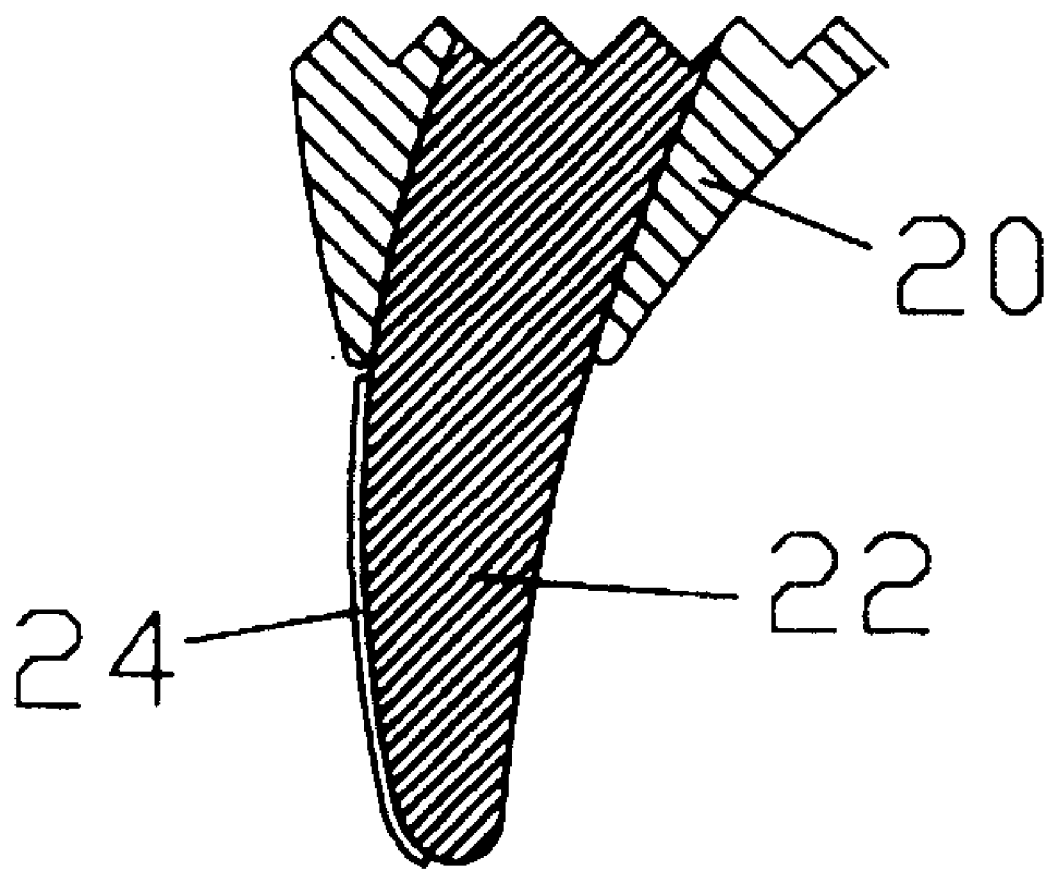
FIG. 6 is a cross-sectional elevation view of a tooth, taken along section line 6—6 of FIG. 5, disclosing the strip of material of the present invention conforming to and adhesively attached to the teeth by means of the oral care substance located between the teeth and the strip of material.

FIGS. 5 and 6 show a delivery system 24 of the present invention applied to a surface of a tooth and plurality of adjacent teeth Embedded in adjacent soft tissue 20 are a plurality of adjacent teeth 22. Adjacent soft tissue is herein defined as soft tissue surfaces surrounding the tooth structure including: papilla, marginal gingiva, gingival sulculus, inter dental gingiva, gingival gum structure on lingual and buccal surfaces up to and including muco-ginival junction and the pallet.

In both FIGS. 5 and 6, delivery system 24 represents strip of material 12 and oral care substance 14, with oral care substance 14 on the side of strip of material 12 facing tooth 22. Oral care substance 14 may be pre-applied to strip of material 12, or applied to strip of material 12 by the delivery system user, or applied directly to the teeth 22 and then covered by strip of material 12. In either case, strip of material 12 has a thickness and flexural stiffness which enable it to conform to the contoured surfaces of tooth 22 and to adjacent soft tissue 20. The strip of flexible material has sufficient flexibility to form to the contours of the oral surface, in this figure the surface being a plurality of adjacent teeth. The strip of material is also readily conformable to tooth surfaces and to the interstitial tooth spaces without permanent deformation when the delivery system is applied. The delivery system is applied without significant pressure.

Figure 7:
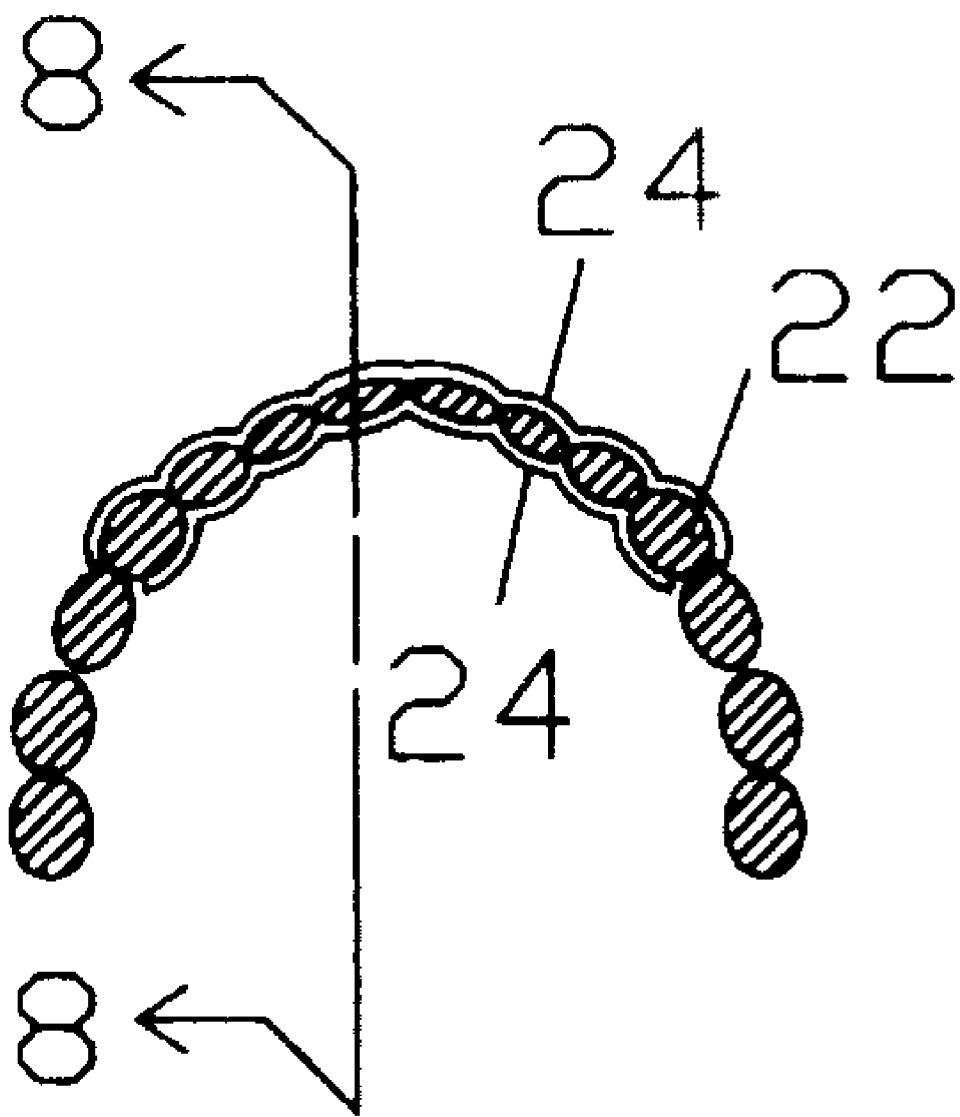
FIG. 7 is a cross-sectional plan view, similar to FIG. 5, showing a strip of material of the present invention conforming to the teeth and the adjoining soft tissue and adhesively attached to both sides of the teeth by means of the oral care substance located between the teeth and the strip of material.
Figure 8:
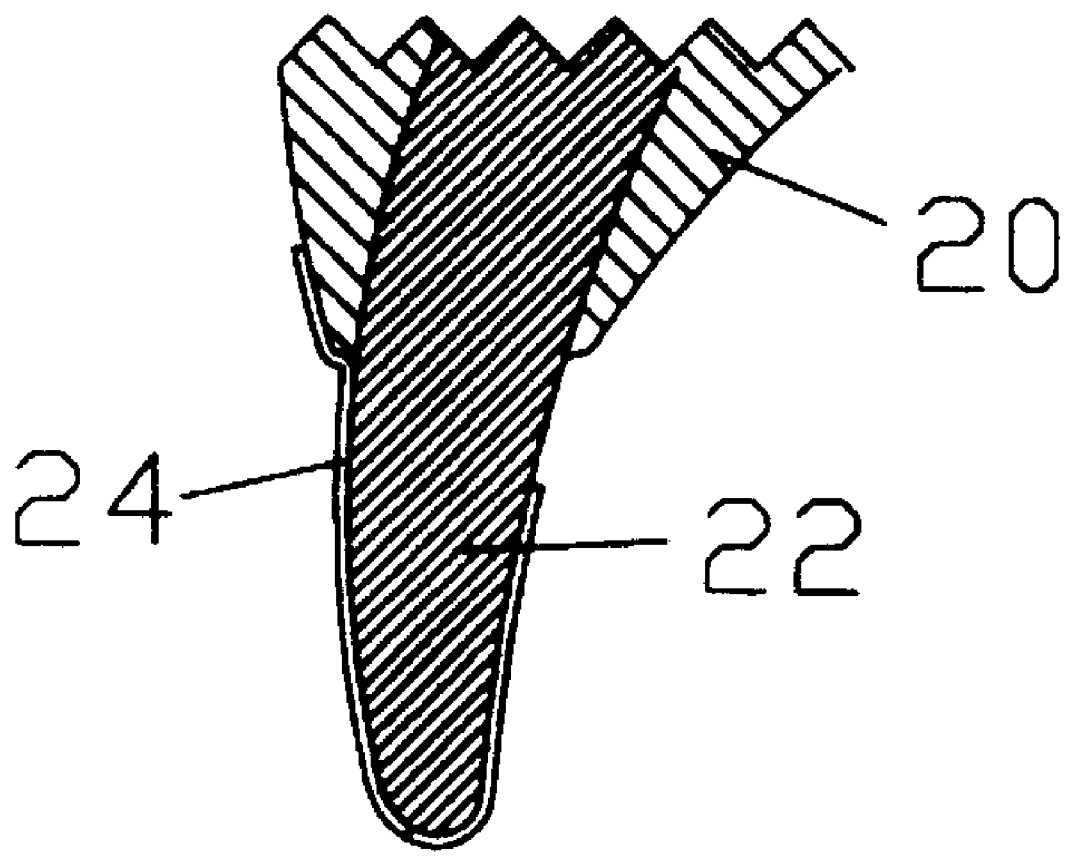
FIG. 8 is a cross-sectional elevation view, taken along section line 8—8 of FIG. 7, showing a strip of material of the present invention conforming to both the tooth and the adjoining soft tissue and adhesively attached to both sides of the tooth by means of the oral care substance located between the tooth and the strip of material.

FIGS. 7 and 8 show a delivery system 24 of the present invention applied to both front and rear surfaces of a plurality of adjacent teeth 22 as well as to adjacent soft tissue 20. Delivery system 24 represents strip of material 12 and oral care substance 14, with oral care substance 14 on the side of strip of material 12 facing tooth 22.

Figure 9:
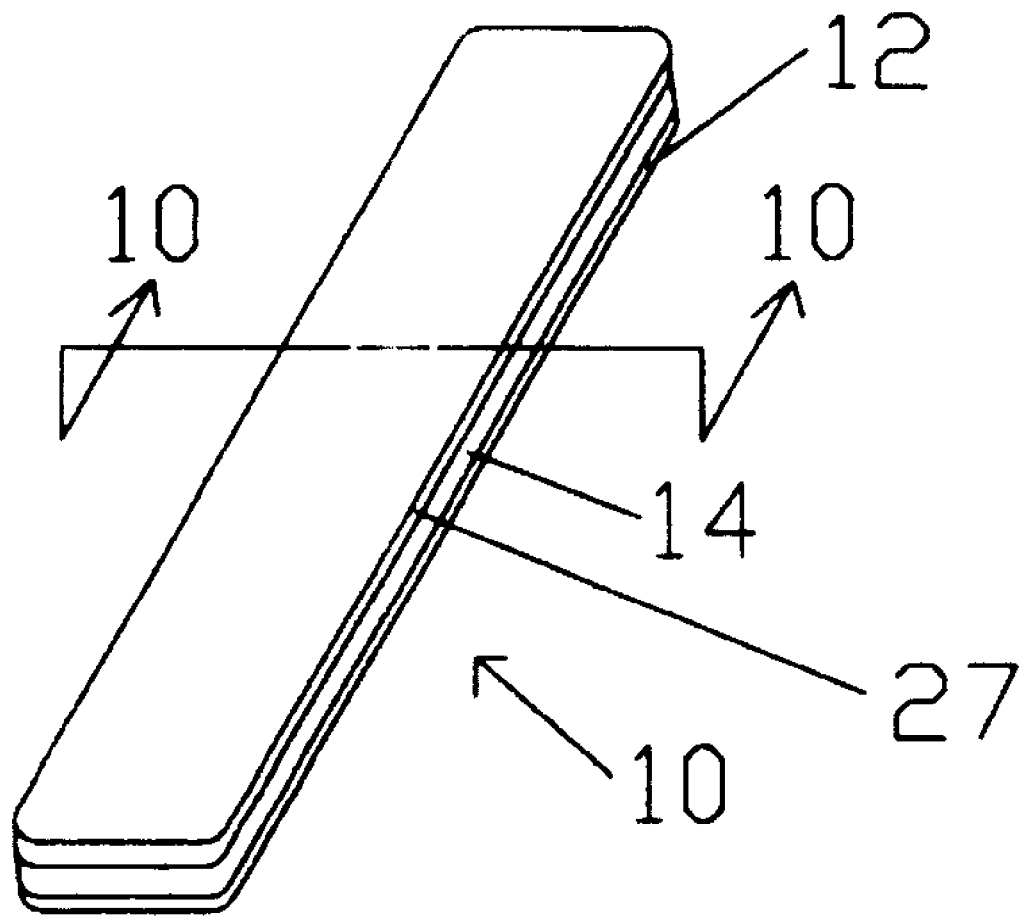
FIG. 9 is a perspective view of an alternative embodiment of the present invention, disclosing the flat strip of material coated with an oral care substance of FIG. 2 for treating teeth and adjoining soft tissue having a release liner.
Figure 10:
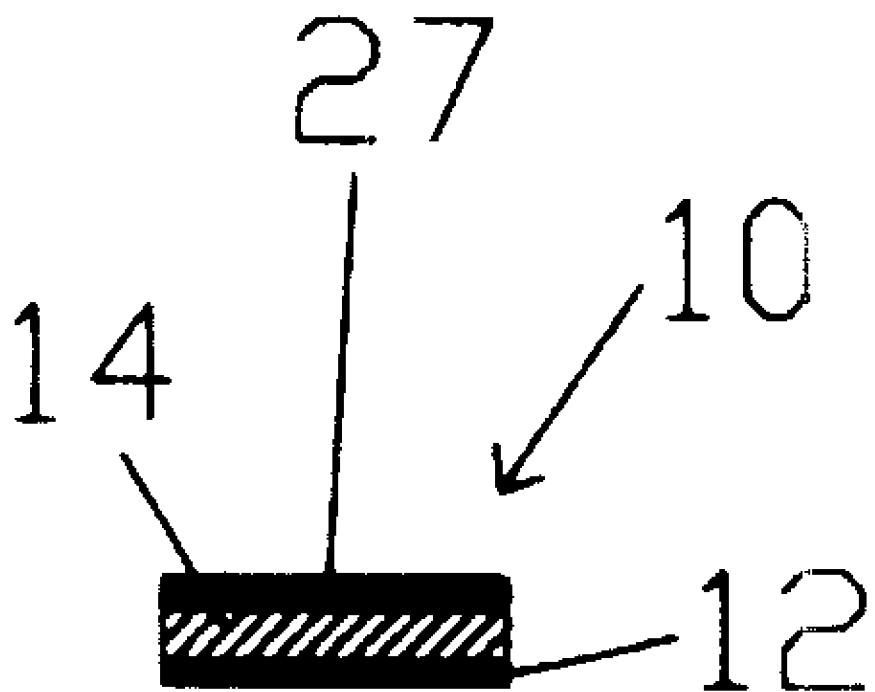
FIG. 10 is a cross-sectional view of an alternative embodiment of the present invention, taken along section line 10—10 of FIG. 9, showing a release liner attached to the strip of material by the oral care substance on the strip of material.

FIGS. 9 and 10 shows optional release liner 27. Release liner 27 is attached to strip of material 12 by oral care substance 14. Oral care substance 14 is on the side of strip of material 12 facing release liner 27. This side is applied to the tooth and gum surfaces once release liner 27 is removed.

Strip of Material

The strip of material serves as a protective barrier for the oral care substance. It prevents substantial leaching and/or erosion of the oral care substance by for example, the wearer's lips, tongue, as well as saliva. This allows the active in the oral care composition to act upon the oral surface for an extended period of time, from several minutes to several hours. The term "act upon" is herein defined as bringing about a desired change. For example, if the oral care substance is an anti-microbial substance, it reduces or eliminates proliferation of microbial growth that has an overall positive impact on the oral cavity including teeth and gingival tissue.

The strip of material may comprise polymers, natural and synthetic woven materials, non-woven material, foil, paper, rubber, and combinations thereof. The strip of material may be a single layer of material or a laminate of more than one layer. Regardless of the number of layers, the strip of material is substantially water impermeable. Preferably, the material is any type of polymer or combination of polymers that meet the required flexural rigidity and are compatible with oral care substances. Suitable polymers include, but are not limited to, polyethylene, ethylvinylacetate, polyesters, ethylvinyl alcohol and combinations thereof. Examples of polyesters include Mylar® and fluoroplastics such as Teflon®, both manufactured by DuPont. The preferable material is polyethylene. The strip of material is generally less than about 1 mm thick, preferably less than about 0.05 mm thick, and more preferably from about 0.001 to about 0.03 mm thick. A polyethylene strip of material is preferably less than about 0.1 mm thick and more preferably from about 0.005 to about 0.02 mm thick.

The shape of the strip of material is any shape and size that covers the desired oral surface. Preferably the strip of material has rounded corners. Rounded corners is defined as not having any sharp angles or points. In one example, the length of the strip of material is from about 2 cm to about 12 cm and preferably from about 4 cm to about 9 cm. The width of the strip of material will also depend upon the oral surface area to be covered. In one example, the width of the strip of material is from about 0.5 cm to about 4 cm and preferably from about 1 cm to about 2 cm.

The strip of material may contain shallow pockets. When the oral care substance is coated on a strip of material, additional oral care substance fills shallow pockets to provide reservoirs of additional oral care substance. Additionally, the shallow pockets help to provide texture to the delivery system. The film will preferably have an array of shallow pockets. Generally, the shallow pockets are approximately 0.4 mm across and 0.1 mm deep. When shallow pockets are included in the strip of material and oral care substances are applied to it in various thicknesses, the overall thickness of the delivery system is generally less than about 1 mm. Preferably, the overall thickness is less than about 0.5 mm.

Flexural stiffness is a material property that is a function of a combination of strip thickness, width, and material modulus of elasticity. This test is a method for measuring the rigidity of polyolefin film and sheeting. It determines the resistance to flexure of a sample by using a strain gauge affixed to the end of a horizontal beam. The opposite end of the beam presses across a strip of the sample to force a portion of the strip into a vertical groove in a horizontal platform upon which the sample rests. A microammeter, wired to the strain gauge is calibrated in grams of deflection force. The rigidity of the sample is read directly from the microammeter and expressed as grams per centimeter of sample strip width. In the present invention, the strip of material has a flexural stiffness of less than about 5 grams/cm as measured on a Handle-O-Meter, model #211–300, available from Thwing-Albert Instrument Co. of Philadelphia, Pa., as per test method ASTM D2923-95. Preferably, the strip of material has a flexural stiffness less than about 3 grams/cm, more preferably less than about 2 grams/cm, and most preferably from about 0.1 grams/cm to about 1 grams/cm. Preferably, the flexural stiffness of the strip of material is substantially constant and does not change during normal use. For example, the strip of material does not need to be hydrated for the strip to achieve the low flexural stiffness in the above-specified ranges.

This relatively low stiffness enables the strip of material to cover the contours of the oral surface with very little force being exerted. That is, conformity to the contours of the oral surface of the wearer's mouth is maintained because there is little residual force within the strip of material to cause it to return to its shape just prior to its application to the oral surface, i.e. substantially flat. The strip of material's flexibility enables it to contact soft tissue over an extended period of time without irritation. The strip of material does not require pressure forming it against the oral surface.

The strip of material is held in place on the oral surface by adhesive attachment provided by the oral care substance. The viscosity and general tackiness of the oral care substance cause the strip of material to be adhesively attached to the oral surface without substantial slippage from the frictional forces created by the lips, teeth, tongue and other oral surfaces rubbing against the strip of material while talking, drinking, etc. However, this adhesion to the oral surface is low enough to allow the strip of material to be easily removed by the wearer by simply peeling off the strip of material using ones finger, fingernail or rubbing with a soft implement such as a cotton balls and swabs or gauze pads. The delivery system is easily removable from the oral surfaces without the use of an instrument, a chemical solvent or agent or excessive friction. The chemical solvents include organic solvent known for use in the oral cavity such as alcohols, and other safe solvents such as water, that can be used to dilute the gelling agent.

The peel force required to remove the strip of material from the oral surface is from about 1 gram to about 50 grams for a 1.5 cm strip width (approximately 17 grams/cm) is all that is required. Preferably, the peel force is from about 10 grams to about 40 grams and more preferably from about 20 grams to about 30 grams. The low peel force is desired for consumer handling purposes. The low peel force is possible because of the non-aggressive nature of the oral care substance necessary to adhere the strip of material having lower flexural stiffness. That is a strip of material having high flexural stiffness higher would require an aggressive adhesive to stop the strip of material from pulling it away from the contours of the oral surface it is attached to.

The strip of material may be formed by several of the film making processes known in the art. Preferably, a strip of material made of polyethylene is made by a blown process or a cast process. Other processes, including extrusion or processes that do not affect the flexural rigidity of the strip of material are also feasible. Additionally, the oral care substance may be incorporated onto the strip during the processing of the strip. The oral care substance may be a laminate on the strip.

Oral Care Substances

The oral care substance preferably contains an active at a level where upon directed use, promotes the benefit sought by the wearer without detriment to the oral surface it is applied to. Examples of the oral conditions these actives address include, but, are not limited to appearance and structural changes to teeth, whitening, stain bleaching, stain removal, plaque removal, tartar removal, cavity prevention and treatment, inflamed and, or bleeding gums, mucosal wounds, lesions, ulcers, aphthous ulcers, cold sores tooth abscesses, and the elimination of mouth malodor resulting from the conditions above and other causes such as microbial proliferation.

The amount of oral care substance applied to the strip of material or oral surface depends upon the size and capacity of the piece of material, concentration of the active, and the desired benefit sought. Generally, less than about 1 gram of oral care substance is required. Preferably, from about 0.05 grams to about 0.5 grams and more preferably from about 0.1 gram to about 0.4 grams of the oral care substance is used. The amount of oral care substance per square cm of material is less than about 0.2 grams/cm$^2$, preferably from about 0.005 to about 0.1 grams/cm$^2$, and more preferably from about 0.01 grams/cm$^2$ to about 0.04 grams/cm$^2$.

The oral care substance of the present invention can be in the form of a viscous liquid, paste, gel, solution, or other suitable that can provide sufficient adhesion. Preferably, the oral care substance is in the form of a gel. The oral care substance will have a viscosity of from about 200 to about 1,000,000 cps at low shear rates (less than one 1/seconds). Preferably, the viscosity is from about 100,000 to about 800,000 cps and more preferably from about 400,000 to about 600,000 cps.

Oral Care Actives

Suitable for oral care actives include any material that is generally considered as safe for use in the oral cavity that provides changes to the overall health of the oral cavity, and specifically the condition of the oral surfaces the oral care substance contacts. The level of oral care substance in the present invention is from about 0.01% to about 40%, preferably from about 0.1% to about 20%, more preferably from about 0.5% to about 10%, and most preferably from about 1% to about 7%, by weight of the oral care substance.

Oral care compositions or substances of the present invention may include many of the actives previously disclosed in the art. The following is a non all-inclusive list of oral care actives that may be used in the present invention.

1. Teeth Whitening Actives

Teeth whitening actives may be included in the oral care substance of the present invention. The actives suitable for whitening are selected from the group consisting of the peroxides, metal chlorites, perborates, percarbonates, peroxyacids, and combination thereof. Suitable peroxide compounds include hydrogen peroxide, calcium peroxide, carbamide peroxide, and mixtures thereof. Most preferred is carbamide peroxide. Suitable metal chlorites include calcium chlorite, barium chlorite, magnesium chlorite, lithium chlorite, sodium chlorite, and potassium chlorite. Additional whitening actives may be hypochlorite and chlorine dioxide. The preferred chlorite is sodium chlorite.

2. Phosphates

Anti-tartar agents known for use in dental care products includes phosphates. Phosphates include pyrophosphates, polyphosphates, polyphosphonates and mixtures thereof. Pyrophosphates are among the best known for use in dental care products. Pyrophosphate ions are delivered to the teeth derive from pyrophosphate salts. The pyrophosphate salts useful in the present compositions include the dialkali metal pyrophosphate salts, tetra-alkali metal pyrophosphate salts, and mixtures thereof. Disodium dihydrogen pyrophosphate ($Na_2H_2P_2O_7$, tetrasodium pyrophosphate ($Na_4P_2O_7$, and tetrapotassium pyrophosphate ($K_4P_2O_7$ in their unhydrated as well as hydrated forms are the preferred species. While any of the above mentioned pyrophosphate salts may be used, tetrasodium pyrophosphate salt is preferred.

The pyrophosphate salts are described in more detail in Kirk & Othmer, Encyclopedia of Clinical Technology Third Edition, Volume 17, Wiley-Interscience Publishers (1982), incorporated herein by reference in its entirety, including all references incorporated into Kirk & Othmer. Additional anticalculus agents include pyrophosphates or polyphosphates disclosed in U.S. Pat. No. 4,590,066 issued to Parran & Sakkab on May 20, 1986; polyacrylates and other polycarboxylates such as those disclosed in U.S. Pat. No. 3,429,963 issued to Shedlovsky on Feb. 25, 1969 and U.S. Pat. No. 4,304,766 issued to Chang on Dec. 8, 1981; and U.S. Pat. No. 4,661,341 issued to Benedict & Sunberg on Apr. 28, 1987; polyepoxysuccinates such as those disclosed in U.S. Pat. No. 4,846,650 issued to Benedict, Bush & Sunberg on Jul. 11, 1989; ethylenediaminetetraacetic acid as disclosed in British Patent No. 490,384 dated Feb. 15, 1937; nitrilotriacetic acid and related compounds as disclosed in U.S. Pat. No. 3,678,154 issued to Widder & Briner on Jul. 18, 1972; polyphosphonates as disclosed in U.S. Pat. No. 3,737,533 issued to Francis on Jun. 5,1973, U.S. Pat. No. 3,988,443 issued to Ploger, Schmidt-Dunker & Gloxhuber on Oct. 26, 1976 and U.S. Pat. No. 4,877,603 issued to Degenhardt & Kozikowski on Oct. 31, 1989; all of these patents are incorporated herein by reference. Anticalculus phosphates include potassium and sodium pyrophosphates; sodium tripolyphosphate; diphosphonates, such as ethane-1-hydroxy-1,1-diphosphonate, 1-azacycloheptane-1,1-diphosphonate, and linear alkyl diphosphonates; linear carboxylic acids; and sodium zinc citrate.

Agents to may be used in place of or in combination with the pyrophosphate salt include such known materials as synthetic anionic polymers including polyacrylates and copolymers of maleic anhydride or acid and methyl vinyl ether (e.g., Gantrez), as described, for example, in U.S. Pat. No. 4,627,977, to Gaffar et al., the disclosure of which is incorporated herein by reference in its entirety; as well as, e.g., polyamino propoane sulfonic acid (AMPS), zinc citrate trihydrate, polyphosphates (e.g., tripolyphosphate; hexametaphosphate), diphosphonates (e.g., EHDP; AHP), polypeptides (such as polyaspartic and polyglutamic acids), and mixtures thereof.

3. Fluoride Ion Source

Fluoride ion sources are well know for use in oral care compositions as anticaries agents. Fluoride ions are contained in a number of oral care compositions for this purpose, particularly toothpastes. Patents disclosing such toothpastes include U.S. Pat. No. 3,538,230, Nov. 3, 1970 to Pader et al; U.S. Pat. No. 3,689,637, Sep. 5, 1972 to Pader; U.S. Pat. No. 3,711,604, Jan. 16, 1973 to Colodney et al; U.S. Pat. No. 3,911,104, Oct. 7, 1975 to Harrison; U.S. Pat. No. 3,935,306, Jan. 27, 1976 to Roberts et al; and U.S. Pat. No. 4,040,858, Aug. 9, 1977 to Wason.

Application of fluoride ions to dental enamel serves to protect teeth against decay. A wide variety of fluoride ion-yielding materials can be employed as sources of soluble fluoride in the instant compositions. Examples of suitable fluoride ion-yielding materials are found in Briner et al; U.S. Pat. No. 3,535,421; issued Oct. 20, 1970 and Widder et al; U.S. Pat. No. 3,678,154; issued Jul. 18, 1972, both patents being incorporated herein by reference. Preferred fluoride ion sources for use herein include sodium fluoride, potassium fluoride and ammonium fluoride. Sodium fluoride is particularly preferred. Preferably the instant compositions provide from about 50 ppm to 10,000 ppm, more preferably from about 100 to 3000 ppm, of fluoride ions in the aqueous solutions that contact dental surfaces when used with the strip of material used in the mouth.

4. Antimicrobial Agents

Antimicrobial agents can also be present in the oral care compositions or substances of the present invention. Such agents may include, but are not limited to, 5-chloro-2-(2,4-dichlorophenoxy)-phenol, commonly referred to as triclosan, and described in The Merck Index, 11th ed. (1989), pp. 1529 (entry no. 9573) in U.S. Pat. No. 3,506,720, and in European Patent Application No. 0,251,591 of Beecham Group, PLC, published Jan. 7, 1988; phthalic acid and its salts including, but not limited to those disclosed in U.S. Pat. No. 4,994,262, Feb. 19, 1991, substituted monoperthalic acid and its salts and esters as disclosed in U.S. Pat. Nos. 4,990,329, Feb. 5, 1991, 5,110,583, May 5, 1992 and 4,716,035, Dec. 29, 1987, all to Sampathkumar; preferably magnesium monoperoxy phthalate, chlorhexidine (Merck Index, no. 2090), alexidine (Merck Index, no. 222; hexetidine (Merck Index, no. 4624); sanguinarine (Merck Index, no. 8320); benzalkonium chloride (Merck Index, no. 1066); salicylanilide (Merck Index, no. 8299); domiphen bromide (Merck Index, no. 3411); cetylpyridinium chloride (CPC) (Merck Index, no. 2024; tetradecylpyridinium chloride (TPC); N-tetradecyl-4-ethylpyridinium chloride (TDEPC); octenidine; delmopinol, octapinol, and other piperidino derivatives; nicin preparations; zinc/stannous ion agents; antibiotics such as augmentin, amoxicillin, tetracycline, doxycycline, minocycline, and metronidazole; and analogs and salts of the above; essential oils including thymol, geraniol, carvacrol, citral, hinokitiol, eucalyptol, catechol (particularly 4-allyl catechol) and mixtures thereof; methyl salicylate; hydrogen peroxide; metal salts of chlorite and mixtures of all of the above.

5. Anti-inflammatory Agents

Anti-inflammatory agents can also be present in the oral care compositions or substances of the present invention. Such agents may include, but are not limited to, non-steroidal anti-inflammatory agents or NSAIDs such as ketorolac, flurbiprofen, ibuprofen, naproxen, indomethacin, aspirin, ketoprofen, piroxicam and meclofenamic acid. Use of NSAIDs such as Ketorolac are claimed in U.S. Pat. No. 5,626,838, issued May 6, 1997, herein incorporated by reference. Disclosed therein are methods of preventing and, or treating primary and reoccurring squamous cell carcinoma of the oral cavity or oropharynx by topical administration to the oral cavity or oropharynx an effective amount of an NSAID.

6. Nutrients

Nutrients may improve the condition of the oral cavity and can be included in the oral care compositions or substances of the present invention. Nutrients include minerals, vitamins, oral nutritional supplements, enteral nutritional supplements, and mixtures thereof.

Minerals that can be included with the compositions of the present invention include calcium, phosphorus, fluoride, zinc, manganese, potassium and mixtures thereof. These minerals are disclosed in Drug Facts and Comparisons (loose leaf drug information service), Wolters Kluer Company, St. Louis, Mo., 1997, pp 10–17; incorporated herein by reference.

Vitamins can be included with minerals or used separately. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Such vitamins are disclosed in Drug Facts and Comparisons (loose leaf drug information service), Wolters Kluer Company, St. Louis, Mo., 1997, pp. 3–10; incorporated herein by reference.

Oral nutritional supplements include amino acids, lipotropics, fish oil, and mixtures thereof, as disclosed in Drug Facts and Comparisons (loose leaf drug information service), Wolters Kluer Company, St. Louis, Mo., 1997, pp. 54–54e; incorporated herein by reference. Amino acids include, but, are not limited to L-Tryptophan, L-Lysine, Methionine, Threonine, Levocarnitine or L-carnitine and mixtures thereof. Lipotropics include, but, are not limited to choline, inositol, betaine, linoleic acid, linolenic acid, and mixtures thereof. Fish oil contains large amounts of Omega-3 (N-3) Polyunsaturated fatty acids, eicosapentaenoic acid and docosahexaenoic acid.

Entenal nutritional supplements include, but, are not limited to protein products, glucose polymers, corn oil, safflower oil, medium chain triglycerides as disclosed in Drug Facts and Comparisons (loose leaf drug information service), Wolters Kluer Company, St. Louis, Mo., 1997, pp. 55–57; incorporated herein by reference.

7. Enzymes

An individual or combination of several compatible enzymes can be included in the oral care composition or substance of the present invention. Enzymes are biological catalysts of chemical reactions in living systems. Enzymes combine with the substrates on which they act forming an intermediate enzyme-substrate complex. This complex is then converted to a reaction product and a liberated enzyme which continues its specific enzymatic function.

Enzymes provide several benefits when used for cleansing of the oral cavity. Proteases break down salivary proteins which are absorbed onto the tooth surface and form the pellicle; the first layer of resulting plaque. Proteases along with lipases destroy bacteria by lysing proteins and lipids which form the structural component of bacterial cell walls and membranes. Dextranases break down the organic skeletal structure produced by bacteria that forms a matrix for bacterial adhesion. Proteases and amylases, not only present plaque formation, but also prevent the development of calculus by breaking-up the carbohydrate-protein complex that binds calcium, preventing mineralization.

Enzymes useful in the present invention include any of the commercially available proteases, glucanohydrolases, endoglycosidases, amylases, mutanases, lipases and mucinases or compatible mixtures thereof. Preferred are the proteases, dextranases, endoglycosidases and mutanases, most preferred being papain, endoglycosidase or a mixture of dextranase and mutanase. Additional enzymes suitable for use in the present invention are disclosed in U.S. Pat. No. 5,000,939 to Dring et al., Mar. 19, 1991; U.S. Pat. No. 4,992,420 to Neeser, Feb. 12, 1991; U.S. Pat No. 4,355,022 to Rabussay, Oct. 19, 1982; U.S. Pat. No. 4,154,815 to Pader, May 15, 1979; U.S. Pat. No. 4,058,595 to Colodney, Nov. 15, 1977; U.S. Pat. No. 3,991,177 to Virda et al., Nov. 9, 1976 and U.S. Pat. No. 3,696,191 to Weeks, Oct. 3, 1972; all incorporated herein by reference.

8. Mouth and Throat Products

Other materials that can be used with the present invention include commonly known mouth and throat products. Such products are disclosed in Drug Facts and Comparisons (loose leaf drug information service), Wolters Kluer Company, St. Louis, Mo., 1997, pp. 520b–527; incorporated herein by reference. These products include, but, are not limited to anti-fungal, antibiotic and analgesic agents.

9. Antioxidants

Antioxidants are generally recognized as useful in compositions such as those of the present invention. Antioxidants are disclosed in texts such as Cadenas and Packer, The Handbook of Antioxidants©, 1996 by Marcel Dekker, Inc., incorporated herein by reference. Antioxidants that may be included in the oral care composition or substance of the present invention include, but are not limited to Vitamin E, ascorbic acid, Uric acid, carotenoids, Vitamin A, flavonoids and polyphenols, herbal antioxidants, melatonin, aminoindoles, lipoic acids and mixtures thereof.

10. H-2 Antagonists

Histamine-2 (H-2 or $H_2$) receptor antagonist compounds (H-2 antagonists) may be used in the oral care composition of the present invention. As used herein, selective H-2 antagonists are compounds that block H-2 receptors, but do not have meaningful activity in blocking histamine-1 (H-1 or $H_1$) receptors. Selective H-2 antagonists stimulates the contraction of smooth muscle from various organs, such as the gut and bronchi; this effect can be suppressed by low concentrations of mepyramine—a typical antihistaminic drug. The pharmacological receptors involved in these mepyramine-sensitive histamine responses have been defined as H-1 receptors (Ash, A. S. F. & H. O. Schild, Brit. J. Pharmacol Chemother., Vol. 27 (1966), p. 427, incorporated herein by reference). Histamine also stimulates the secretion of acid by the stomach (Loew, E. R. & O. Chickering, Proc. Soc. Exp. Biol. Med., Vol. 48 (1941), p. 65, incorporated herein by reference), increases the heart rate (Trendelenburg, U., J. Pharmacol., Vol. 130 (1960), p. 450, incorporated herein by reference), and inhibits contractions in the rat uterus (Dews, P. B. & J. D. P. Graham, Brit. J. Pharmacol. Chemother., Vol. 1 (1946), p. 278, incorporated herein by reference); these actions cannot be antagonized by mepyramine and related drugs. The H-2 antagonists useful in the oral care compositions or substances are those that blockade the receptors involved in mepyramine-insensitive, non-H-1 (H-2), histamine responses, and do not blockade the receptors involved in mepyramine-sensitive histamine responses.

Selective H-2 antagonists are those compounds found to be H-2 antagonists through their performance in classical preclinical screening tests for H-2 antagonist function. Selective H-2 antagonists are identified as compounds which can be demonstrated to function as competitive or non-competitive inhibitors of histamine-mediated effects in those screening models specifically dependent upon H-2 receptor function, but to lack significant histamine antagonist activity in those screening models dependent upon H-1 receptor function. Specifically, this includes compounds that would be classified as described by Black, J. W., W. A. M. Duncan, C. J. Durant, C. R. Ganellin & E. M. Parsons, "Definition and Antagonism of Histamine $H_2$-Receptors", Nature, Vol. 236 (Apr. 21, 1972), pp. 385–390 (Black), incorporated herein by reference, as H-2 antagonists if assessed as described by Black through testing with the guinea pig spontaneously beating right atria in vitro assay and the rat gastric acid secretion in vivo assay, but shown to lack in significant H-1 antagonist activity relative to H-2 antagonist activity, if assessed as described by Black with either the guinea pig ileum contraction in vitro assay or the rat stomach muscle contraction in vivo assay. Preferably selective H-2 antagonists demonstrate no significant H-1 activity at reasonable dosage levels in the above H-1 assays. Typical reasonable dosage level is the lowest dosage level at which 90% inhibition of histamine, preferably 99% inhibition of histamine, is achieved in the above H-2 assays.

Selective H-2 antagonists include compounds meeting the above criteria which are disclosed in U.S. Pat. Nos. 5,294,433 and 5,364,616 Singer et al., issued Mar. 15, 1994 and Nov. 15, 1994 respectively and assigned to Procter & Gamble; both herein incorporated by reference. wherein the selective H-2 antagonist is selected from the group consisting of cimetidine, etintidine, ranitidine, ICIA-5165, tiotidine, ORF-17578, lupitidine, donetidine, famotidine, roxatidine, pifatidine, lamtidine, BL-6548, BMY-25271, zaltidine, nizatidine, mifentidine, BMY-52368, SKF-94482, BL-6341A, ICI-162846, ramixotidine, Wy-45727, SR-58042, BMY-25405, loxtidine, DA-4634, bisfentidine, sufotidine, ebrotidine, HE-30-256, D-16637, FRG-8813, FRG-8701, impromidine, L-643728, and HB-408.4. Particularly preferred is cimetidine (SKF-92334), N-cyano-N'-methyl-N"-(2-(((5-methyl-1H-imidazol-4-yl)methyl)thio)ethyl)guanidine:

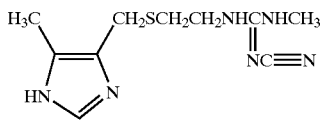

Cimetidine is also disclosed in the Merck Index, 11th edition (1989), p. 354 (entry no. 2279), and Physicians' Desk Reference, 46th edition (1992), p. 2228. Related preferred H-2 antagonists include burimamide and metiamide.

As previously mentioned, the oral care substance of the present invention can be in a variety forms, but, most preferable is a gel, particularly an aqueous gel. The gel is a high viscosity matrix formed from gelling agents known in the art. These gelling agents are safe for oral use, do not readily dissolve in saliva, and do not react with or inactivate the oral care compounds incorporated into them. Generally, the gelling agent is a swellable polymer. Furthermore, the gel formed with these agents provide sufficient adhesive attachment of the film material to the targeted area of the mouth. The level of gelling agent to form the gel composition is from about 0.1% to about 15%, preferably from about 1% to about 10%, more preferably from about 2% to about 8%, and most preferably from about 4% to about 6%, by weight of the oral care composition or substance.

Suitable gelling agents useful in the present invention include carboxypolymethylene, carboxymethyl cellulose, carboxypropyl cellulose, polyoxamers, carrageenan, Veegum, carboxyvinyl polymers, and natural gums such as gum karaya, xanthan gum, Guar gum, gum arabic, gum tragacanth, and mixtures thereof. The preferable gelling agent for use in the present invention is carboxypolymethylene, obtained from B. F. Goodrich Company under the tradename Carbopol®. Particularly preferable Carbopols include Carbopol 934, 940, 941, 956 and mixtures thereof. Particularly preferred is Carbopol 956. Carboxypolymethylene is a slightly acidic vinyl polymer with active carboxyl groups. The normal concentration of various carboxypolymethylene resins in water, according to the manufacturer, is below about 2%. However, it has been found that by preparing supersaturated carboxypolymethylene compositions having an absolute concentration in the ranges specified above, suitable high viscosity oral gel compositions may be prepared.

The concentrated carboxypolymethylene gels have a number of important characteristics in addition to high viscosity. Enough carboxypolymethylene is added to the oral gel compositions beyond that required to provide high viscosity such that a significant quantity of saliva or water is required to lower the viscosity to the point that the composition may be diluted and washed out by saliva. The concentrated carboxypolymethylene composition also has a unique tackiness or stickiness which retains and seals the strip material against the targeted oral cavity surface it is affixed to, particularly teeth. However, care should be taken to avoid too much carboxypolymethylene thereby making insertion or withdrawal of the strip material difficult.

If the oral care substance is an aqueous gel, the water present in the gel compositions should preferably be deionized and free of organic impurities. Water comprises from about 0.1% to 95%, preferably from about 5% to about 90%, and most preferably from about 10% to about 80%, by weight of the oral care substance. This amount of water includes the free water that is added plus that amount that is introduced with other materials.

A pH adjusting agent may also be added to optimize the storage stability of the gel and to make the substance safe for oral tissue. These pH adjusting agents, or buffers, can be any material which is suitable to adjust the pH of the oral care substance. Suitable materials include sodium bicarbonate, sodium phosphate, sodium hydroxide, ammonium hydroxide, sodium stannate, triethanolamine, citric acid, hydrochloric acid, sodium citrate, and combinations thereof. The pH adjusting agents are added in sufficient amounts so as to adjust the pH of the gel composition to about 4.5 to about 11, preferably from about 5.5 to about 8.5, and more preferably from about 6 to about 7. pH adjusting agents are generally present in an amount of from about 0.01% to about 15% and preferably from about 0.05% to about 5%, by weight of the oral care substance.

While the gel described above provides sufficient adhesiveness, additional gelling agents may also be included in the formula to help the active ingredients adhere to the tissues of the oral cavity. Suitable agents include both polymers with limited water solubility as well as polymers lacking water solubility. These polymers deposit a thin film on both the oral cavity's soft and hard tissues when saliva combines with the instant composition. Suitable limited water solubility adhesives include: hydroxy ethyl or propyl cellulose. Adhesives lacking water solubility include: ethyl cellulose and polyox resins. Another possible adhesive suitable for use in the instant composition is polyvinylpyrrolidone with a molecular weight of about 50,000 to about 300,000. Still another possible adhesive suitable for use in the instant composition is a combination of Gantrez and the semisynthetic, water-soluble polymer carboxymethyl cellulose.

An additional carrier material may also be added to the oral care substance. Carrier materials can be humectants. Suitable humectants include glycerin, sorbitol, polyethylene glycol, propylene glycol, and other edible polyhydric alcohols. Humectants are generally present in an amount of from about 10% to about 95% and preferably from about 50% to about 80%, by weight of the oral care substance or composition. In addition to the above materials of the gel of the present invention, a number of other components can also be added to the oral care substance. Additional components include, but are not limited to, flavoring agents, sweetening agents, xylitol, opacifiers, coloring agents, and chelants such as ethylenediaminetetraacetic acid. These additional ingredients can also be used in place of the compounds disclosed above.

The Release Liner

The release liner may be formed from any material which exhibits less affinity for the oral care substance than the oral care substance exhibits for itself and for the strip of material. The release liner preferably comprises a rigid sheet of material such as polyethylene, paper, polyester, or other material which is then coated with a non-stick type material. The release liner material may be coated with wax, silicone, teflon, fluoropolymers, or other non-stick type materials. A preferred release liner is Scotchpak® produced by 3M. The release liner may be cut to substantially the same size and shape as the strip of material or the release liner may be cut larger than the strip of material to provide a readily accessible means for separating the material from the strip. The release liner may be formed from a brittle material which cracks when the strip is flexed or from multiple pieces of material or a scored piece of material. Alternative, the release liner may be in two overlapping pieces such as a typical adhesive strip bandage design. A further description of materials suitable as release agents is found in Kirk-Othmer Encyclopedia of Chemical Technology, Fourth Edition, Volume 21, pp. 207–218, incorporated herein by reference.

EXAMPLES

The strip of material 12 is preferably a 0.013 thick piece of polyethylene film. The film preferably has an array of shallow pockets, typically 0.4 mm across and 0.1 mm deep. The strip of material 12 has a flexural stiffness of about 0.6 grams/centimeter as measured on a Handle-O-Meter, model #211–300, available from Thwing-Albert Instrument Co. of Philadelphia, Pa., as per test method ASTM D2923-95.

An example of a tooth whitener is a gel described as follows: combine 70% glycerin, 5% carboxypolymethylene, 10% carbamide peroxide, and 15% water adjusted to pH 6.5 with sodium hydroxide. Mix until homogeneous. Commercial tooth whiteners, such as Opalescence and Nu-Pro Gold are also operable with the delivery system of the present invention.

An example of an oral gel composition of the subject invention containing H-2 antagonists, made by routine processing methods, comprises mixing 2.50% hydroxyethyl cellulose, 0.09% sodium fluoride, 0.05% sodium saccharin, 1.00% ranitidine, and purified water q.s.

An example of an oral gel composition of the subject invention containing enzymes, made by routine processing methods, comprises 61.814% sorbitol, 0.314% Carbopol 956, 0.534% xantham gum, 1.132% citric acid, 6.291 sodium citrate, 5.033% sodium lauroyl sarcosinate (30% solution), 7.864% endoglycosidase (3.2% solution), 0.305% sodium fluoride, water q.s.

An example of an oral gel composition of the subject invention containing antimicrobial actives, made by routine processing methods, comprises from 21.2% to 21.5% glycerin, 6.0% Carbopol 956, 40.0% propylene glycol, 2.5% sodium hydroxide (50% solution), from 0.1% to 0.3% Triclosan and water q.s.

Method of Use

In practicing the present invention, a strip of material is applied to the desired oral surface by the wearer. The side of the material facing the oral surface is coated with a oral care substance that is preferably in a highly viscous state. This oral care substance provides a vehicle for the active as well as tackiness between the oral surfaces and the strip of material, holding the strip of material in place for extended periods of time. For oral care actives other than teeth whiteners, the period over which the strip of material is used is from about 1 minute to about 8 hours for actives that require long term diffusion into the oral surface, preferably from about 1 to about 120 minutes and most preferably from about 30 to about 60 minutes.

There are many methods using the present invention to reduce or eliminate the proliferation of microbial and bacterial growth in the oral cavity. Such growth is known to be responsible for development of oral conditions including, but not limited to mouth and breath odor, plaque accumulation, gingival inflammation and bleeding of the gum tissue. Prolonged attachment by certain oral bacteria has also been implicated in more progressive periodontal diseases. Numerous articles exist in the literature that describe the advantages of controlling bacterial growth in regard to maintaining good oral well-being of the individual.

Among these methods is one that comprises the steps of first applying a gel comprising an antimicrobial agent, preferably in a highly viscous state, to the strip of material of the present invention. The strip of material with the applied gel is applied to the oral surface, preferably the front surface of a plurality of adjacent teeth and their surrounding gum tissue, with adhesive attachment between the strip of material and the oral surface. This provides sufficient attachment for holding the delivery system in place for a sufficient time to allow the antimicrobial agent to act upon the oral surface. The conformable strip is removed after a period of time for the antimicrobial agent to be effective. Such a period includes from just prior to retiring or upon awakening. Whenever the strip is removed the excess gel residue remaining on the applied surface may be removed by means such as brushing and, or rinsing. Such a method has been found particularly useful in the eliminating mouth odors generated while sleeping.

The strip of material readily conforms to the oral care surface by lightly pressing it there against. The strip of material is easily removed by the wearer by peeling it off using a finger or fingernail. Preferably each successive treatment uses a fresh strip of material.

In the situation were the oral care surface is the surface of teeth, is not unnecessary to prepare the teeth surface before applying the delivery system of the present invention. For example, the wearer may or may not choose to brush his teeth or rinse his mouth before applying the delivery system. The surfaces of the teeth are not required to be dried or to be excessively wet with saliva or water before the strip of material is applied.

Preferably, the strip of material and substances almost unnoticeable when worn, preferably transparent. Thinness of the strip of material may also provide higher temperature of the oral surface wherein the warmer temperature accelerates the rate of diffusion of the active material into the oral surface.

When the wearer removes the strip of material from the tooth, there may be a residual amount of oral care substance remaining on the surface. The amount residual oral care substance, however, will not be great since it has affinity for both the film and for itself. Any residual oral care substance may be easily removed by wiping, brushing or rinsing the oral surface.

While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

What is claimed is:

1. A delivery system for whitening teeth, comprising: a strip of material sized to cover a front surface of a plurality of teeth; a layer of a tooth whitening substance in contact with said strip of material, said tooth whitening substance comprising a gelling agent and a whitening active selected from the group consisting of peroxides, metal chlorites, perborates, percarbonates, peroxyacids, hypochlorites, and combinations thereof; and a release liner having a coating thereon, wherein said release liner exhibits less affinity for said tooth whitening substance than said tooth whitening substance exhibits for itself and for said strip of material.

2. The delivery system of claim 1, wherein said release liner is formed from a rigid sheet of material.

3. The delivery system of claim 1, wherein said gelling agent is selected from the group consisting of carboxypolymethylene, carboxymethyl cellulose, carboxypropyl cellulose, polyoxamers, carrageenan, Veegum, carboxyvinyl polymers, and natural gums.

4. The delivery system of claim 3, wherein said gelling agent is carboxypolymethylene.

5. The delivery system of claim 4, wherein the level of said gelling agent is between about 0.1% and about 15% by weight of said tooth whitening substance.

6. The delivery system of claim 5, wherein the level of said gelling agent is between about 2% and about 8% by weight of said tooth whitening composition.

7. The delivery system of claim 4, wherein said tooth whitening substance further includes water.

8. The delivery system of claim 7, wherein said tooth whitening substance comprises between about 10% and about 80% water by weight of said tooth whitening substance.

9. The delivery system of claim 7, wherein said whitening active is a peroxide.

10. The delivery system of claim 9, wherein said strip of material is formed from polyethylene.

11. A delivery system for whitening teeth, comprising: a flexible strip of material sized to cover a front surface of a plurality of teeth, wherein said strip of material is substantially flat; a thin layer of a tooth whitening substance in contact with said flexible strip of material, said tooth whitening substance comprising a gelling agent and a whitening active selected from the group consisting of peroxides, metal chlorites, perborates, percarbonates, peroxyacids, hypochlorites, and combinations thereof, wherein the level of said gelling agent is between about 0.1% and about 15% by weight of said tooth whitening composition; and a release liner having a coating thereon, wherein said release liner exhibits less affinity for said tooth whitening substance than said tooth whitening substance exhibits for itself and for said flexible strip of material.

12. The delivery system of claim 11, wherein said release liner is formed from a rigid sheet of material.

13. The delivery system of claim 11, wherein said gelling agent is selected from the group consisting of carboxypolymethylene, carboxymethyl cellulose, carboxypropyl cellulose, polyoxamers, carrageenan, Veegum, carboxyvinyl polymers, and natural gums.

14. The delivery system of claim 13, wherein said gelling agent is carboxypolymethylene.

15. The delivery system of claim 14, wherein the level of said gelling agent is between about 2% and about 8% by weight of said tooth whitening composition.

16. The delivery system of claim 13, wherein said tooth whitening substance further includes water.

17. The delivery system of claim 16, wherein said tooth whitening substance comprises between about 10% and about 80% water by weight of said tooth whitening substance.

18. The delivery system of claim 16, wherein said whitening active is a peroxide.

19. The delivery system of claim 18, wherein said flexible strip of material is formed from polyethylene.

20. The delivery system of claim 1, wherein said strip of material is further sized to cover soft tissue adjacent said plurality of teeth.

21. The delivery system of claim 20, wherein the adjacent soft tissue is the marginal gingiva.

22. The delivery system of claim 1, wherein said strip of material is further sized to cover a rear surface of the plurality of teeth.

23. The delivery system of claim 1, wherein said layer of said tooth whitening substance is continuously coated on said strip of material.

* * * * *